(12) United States Patent
Chen et al.

(10) Patent No.: US 9,295,441 B2
(45) Date of Patent: Mar. 29, 2016

(54) BACK-SCATTERING INSPECTION SYSTEMS AND METHODS FOR HUMAN BODY

(71) Applicant: Nuctech Company Limited, Haidian District, Beijing (CN)

(72) Inventors: Zhiqiang Chen, Beijing (CN); Ziran Zhao, Beijing (CN); Yuanjing Li, Beijing (CN); Wanlong Wu, Beijing (CN); Yingkang Jin, Beijing (CN); Li Zhang, Beijing (CN); Le Tang, Beijing (CN); Chenguang Zhu, Beijing (CN); Xianli Ding, Beijing (CN); Xiuwei Chen, Beijing (CN); Ming Ruan, Beijing (CN); Chengcong Xu, Beijing (CN); Xilei Luo, Beijing (CN)

(73) Assignees: Nuctech Company Limited, Haidian District, Beijing (CN); Tsinghua University, Haidian District, Beijing (CN)

( * ) Notice: Subject to any disclaimer, the term of this patent is extended or adjusted under 35 U.S.C. 154(b) by 51 days.

(21) Appl. No.: 14/138,476

(22) Filed: Dec. 23, 2013

(65) Prior Publication Data

US 2014/0185770 A1 Jul. 3, 2014

(30) Foreign Application Priority Data

Dec. 27, 2012 (CN) .......................... 2012 1 0581870

(51) Int. Cl.
*A61B 6/00* (2006.01)
*G01T 1/167* (2006.01)
*G01V 5/00* (2006.01)

(52) U.S. Cl.
CPC ................. *A61B 6/483* (2013.01); *G01T 1/167* (2013.01); *G01V 5/0025* (2013.01)

(58) Field of Classification Search
CPC .............. G01V 5/0025; G01N 23/203; G01N 2223/053; G01N 2223/055; G01N 2223/314; G01N 2223/316; G01N 2223/3301; A61B 6/483
See application file for complete search history.

(56) References Cited

U.S. PATENT DOCUMENTS 6,151,381 A * 11/2000 Grodzins et al. ................ 378/90
2009/0116617 A1 * 5/2009 Mastronardi et al. ........... 378/87

(Continued)

FOREIGN PATENT DOCUMENTS

| WO | WO 2009/067394 A2 | 5/2009 |
| WO | WO 2009/082762 A1 | 7/2009 |
| WO | WO 2012/088810 A1 | 7/2012 |

OTHER PUBLICATIONS

United Kingdom Search and Examination Report for corresponding United Kingdom Patent Application No. GB1322884.6 mailed May 7, 2014.

(Continued)

*Primary Examiner* — Glen Kao
(74) *Attorney, Agent, or Firm* — Merchant & Gould P.C.

(57) ABSTRACT

Human body back-scattering inspection systems and methods are disclosed. In the invention, X-rays modulated by the flying-spot forming unit having spirally distributed flying-spots have a distribution having alternating peaks and valleys on the irradiated surface. In this way, scanning starting times can be precisely controlled to cause two devices to have scanning starting times that are different by a half of a cycle. That is, the beams outputted from one device are at maximum when the beams outputted from the other device are at minimum. In other words, even if the ray source of one device emits rays, it will not significantly affect imaging result of the other device. In such way, the two devices may emit rays and perform scanning at the same time, and thus the total scanning time is reduced.

8 Claims, 4 Drawing Sheets

(56) References Cited

U.S. PATENT DOCUMENTS

| | | |
|---|---|---|
| 2011/0096901 A1 | 4/2011 | Kotowski et al. |
| 2011/0274249 A1 | 11/2011 | Gray et al. |
| 2012/0170716 A1* | 7/2012 | Chen et al. .................... 378/87 |
| 2012/0307968 A1 | 12/2012 | Smith |

OTHER PUBLICATIONS

European Search Report for corresponding European Patent Application No. 13198315.7 mailed Apr. 25, 2014.

* cited by examiner

BACK-SCATTERING INSPECTION SYSTEMS AND METHODS FOR HUMAN BODY

This application claims benefit of Serial No. 201210581870.3, filed 27 Dec. 2012 in China and which application is incorporated herein by reference. To the extent appropriate, a claim of priority is made to each of the above disclosed applications.

TECHNICAL FIELD

The present invention generally relates to radiographic techniques, and more particularly, to back-scattering inspection systems and methods for human body which are capable of accelerating the security inspection.

BACKGROUND

Back-scattering technique is one of the techniques for human body inspection. It scans a human body with beams of X-rays, and receives scattered signals by a large-area detector at the same time. A scattering image of the human body can be obtained through data processing which maps scanning locations to scattered signals.

In the case where a back-scattering device and a human to be scanned both are stationary, one-time scanning can only scan and obtain an image of one side of the human. If a complete inspection is to be performed on the human, the human needs to turn around after scanning of one side, so as to scan the other side.

In order to enhance the efficiency of security inspection, several manufacturers adopted a solution in their back-scattering security inspection systems, in which two back-scattering devices are placed in opposite positions relative to each other so that a human to be scanned stands therebetween when the human is to be scanned. The two back-scattering devices each scan one side of the human body, and thereby there is no need for the human to turn around.

In the case that two devices are placed in opposite positions relative to each other, the two devices typically will not emit beams at the same time. The reason is that if one device emits when the other one is emitting, the one device generates signals on the detector of the other one and thus the scanning image cannot be obtained correctly. Therefore, in the system where two devices stand and scan oppositely, the ray sources in the two devices emit beams in a time-sharing manner, as described in for example Patent Document 1 (CN1019818820A). Thus, a back-scattering system that utilizes time-sharing emission has scanning time that is not less than double of the scanning time of one device.

SUMMARY

In view of one or more problems of the prior art, there is provided human body back-scattering inspection systems and methods thereof which are capable of accelerating the security inspection.

According to an aspect of the invention, there is provided a human body back-scattering inspection system including a first back-scattering scanning device and a second back-scattering scanning device which are placed in opposite positions relative to each other so that an object to be inspected stands therebetween when it is to be scanned, the first back-scattering scanning device including a first X-ray source, a first flying-spot forming unit and a first detector, the first flying-spot forming unit having a plurality of holes that are distributed spirally on its cylindrical surface and outputting beams of X-rays, the first detector receiving beams of X-rays that are reflected from body of the inspected object, the second back-scattering scanning device including a second X-ray source, a second flying-spot forming unit and a second detector, the second flying-spot forming unit having a plurality of holes that are distributed spirally on its cylindrical surface and outputting beams of X-rays, the second detector receiving beams of X-rays that are reflected from body of the inspected object; and a controlling unit coupled to the first and second back-scattering scanning devices, and configured to generate controlling signals to cause the first flying-spot forming unit and the second flying-spot forming unit to output the beams of X-rays at time which is different by a half of a cycle of the intensity of beams varying over time.

According to another aspect of the invention, there is provided a human body back-scattering inspection system including a first back-scattering scanning device and a second back-scattering scanning device which are placed in opposite positions relative to each other so that an object to be inspected stands therebetween when it is to be scanned, the first back-scattering scanning device including a first X-ray source, a first flying-spot forming unit and a first detector, the first flying-spot forming unit outputting beams of X-rays, the first detector receiving beams of X-rays that are reflected from body of the inspected object, the second back-scattering scanning device including a second X-ray source, a second flying-spot forming unit and a second detector, the second flying-spot forming unit outputting beams of X-rays, the second detector receiving beams of X-rays that are reflected from body of the inspected object; and a controlling unit coupled to the first and second back-scattering scanning devices, and configured to generate controlling signals to cause the first and second detectors to collect reflected beams of X-rays in a time-sharing manner.

According to still another aspect of the invention, there is provided a method for use in a human body back-scattering inspection system including a first back-scattering scanning device and a second back-scattering scanning device which are placed in opposite positions relative to each other so that an object to be inspected stands therebetween when it is to be scanned, the first back-scattering scanning device including a first X-ray source, a first flying-spot forming unit and a first detector, the first flying-spot forming unit having a plurality of holes that are distributed spirally on its cylindrical surface and outputting beams of X-rays, the first detector receiving beams of X-rays that are reflected from body of the inspected object, the second back-scattering scanning device including a second X-ray source, a second flying-spot forming unit and a second detector, the second flying-spot forming unit having a plurality of holes that are distributed spirally on its cylindrical surface and outputting beams of X-rays, the second detector receiving beams of X-rays that are reflected from body of the inspected object. The method includes a step of generating controlling signals to cause the first flying-spot forming unit and the second flying-spot forming unit to output the beams of X-rays at time which is different by a half of a cycle of the intensity of beams varying over time.

According to yet another aspect of the invention, there is provided a method for use in a human body back-scattering inspection system including a first back-scattering scanning device and a second back-scattering scanning device which are placed in opposite positions relative to each other so that an object to be inspected stands therebetween when it is to be scanned, the first back-scattering scanning device including a first X-ray source, a first flying-spot forming unit and a first detector, the first flying-spot forming unit outputting beams of X-rays, the first detector receiving beams of X-rays that are reflected from body of the inspected object, the second back-scattering scanning device including a second X-ray source, a second flying-spot forming unit and a second detector, the second flying-spot forming unit outputting beams of X-rays, the second detector receiving beams of X-rays that are reflected from body of the inspected object. The method includes a step of generating controlling signals to cause the first and second detectors to collect reflected beams of X-rays in a time-sharing manner.

According to the embodiments of the invention, two devices can emit beams at the same time even if they are placed in opposite positions, and thus the scanning speed is enhanced.

BRIEF DESCRIPTION OF THE DRAWINGS

The implementations of the invention are illustrated in the drawings. The drawings and implementations provide some embodiments of the invention non-exclusively without limitation, where.

DETAILED DESCRIPTION OF THE EMBODIMENTS

Figure 1:
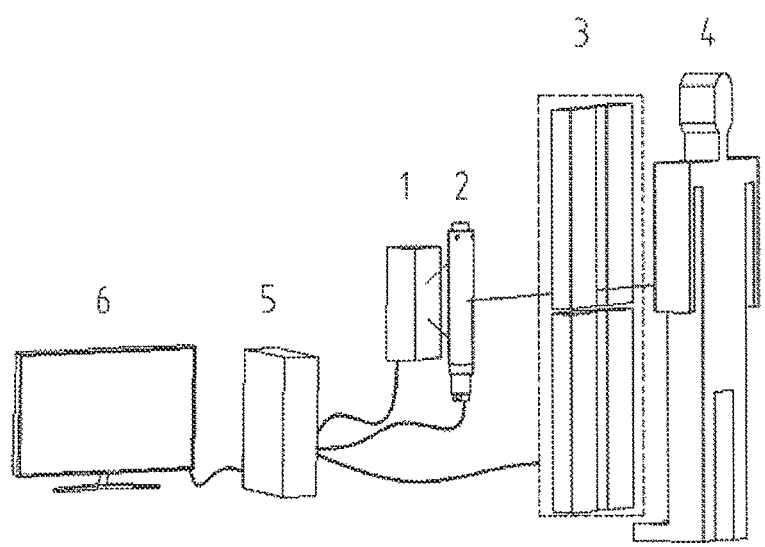
FIG. 1 illustrates a schematic diagram of a scanning device in a human body back-scattering scanning system according to an embodiment of the invention.

The particular embodiments of the invention are described below in details. It shall be noted that the embodiments herein are used for illustration only, but not limiting the invention. In the description below, a number of particular details are explained to provide a better understanding to the invention. However, it is apparent to those skilled in the art the invention can be implemented without these particular details. In other examples, well known circuits, materials or methods are not described so as not to obscure the invention.

Throughout the specification, the reference to "one embodiment," "an embodiment," "one example" or "an example" means that the specific features, structures or properties described in conjunction with the embodiment or example are included in at least one embodiment of the present invention. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

In view of the low scanning speed of the prior art in the case that two back-scattering devices are placed in opposite positions, a human body back-scattering inspection system is provided according to some embodiments of the invention the system includes a first back-scattering scanning device and a second back-scattering scanning device which are placed in opposite positions relative to each other so that an object to be inspected stands therebetween when it is to be scanned. The first back-scattering scanning device includes a first X-ray source, a first flying-spot forming unit and a first detector. The first flying-spot forming unit has a plurality of holes that are distributed spirally on its cylindrical surface and outputs beams of X-rays therefrom. The first detector receives beams of X-rays that are reflected from body of the inspected object. The second back-scattering scanning device includes a second X-ray source, a second flying-spot forming unit and a second detector. The second flying-spot forming unit has a plurality of holes that are distributed spirally on its cylindrical surface and outputs beams of X-rays therefrom. The second detector receives beams of X-rays that are reflected from body of the inspected object. The system further includes a controlling unit coupled to the first and second back-scattering scanning devices and configured to generate controlling signals to cause the first flying-spot forming unit and the second flying-spot forming unit to output the beams of X-rays at time which is different by a half of a cycle of the intensity of beams varying over time. In this way, the flying-spot forming units of the two devices emit beams at different time, and thus the interference to each other is reduced. Therefore, the scanning speed is enhanced while the accuracy of security inspection is maintained.

According to other embodiments of the invention, each of the first and second flying-spot forming units may be not a flying-spot forming unit that uses a scanning manner by means of points spirally distributed on its cylindrical surface, and may be a flying-spot forming unit that emits beams that do not vary over time instead. In such a case, the controlling unit is further configured to be coupled to the first back-scattering scanning device and the second back-scattering scanning device, and to generate controlling signals to cause the first and second detectors to collect reflected beams of X-rays in a time-sharing manner. In this way, the flying-spot forming units of the two devices emit beams emit beams at different time, and thus the interference to each other is reduced. Therefore, the scanning speed is enhanced while the accuracy of security inspection is maintained.

FIG. 1 illustrates a schematic diagram of a scanning device in a human body back-scattering scanning system according to an embodiment of the invention. As shown in FIG. 1, the scanning device in the human body back-scattering scanning system according to the embodiment of the invention includes a ray generator 1, a flying-spot forming unit 2, a back-scattering detector 3, a controlling and data processing terminal 5 and a displaying terminal 6. The human body of to-be-inspected object 4 is to be inspected.

The ray generator 1 emits beams of rays, which are modulated by flying-spot forming unit 2 and form beams of flying-spot rays, then irradiate on the human body of to-be-inspected object 4 and are reflected from the surface of the to-be-inspected object 4. The back-scattering detector 3 receives the reflected beams of rays and generates electrical signals to be outputted to the controlling and data processing terminal 5, which processes the electrical signals to obtain a scanning image to be displayed on the displaying terminal 6.

The foregoing back-scattering human body scanning device typically scans a single side of the human body. If a complete scan is to be performed on the human body, the scanned human needs to turn around after scanning of one side, so as to have the other side to be scanned. In order to remove the inconvenience, there is proposed a solution in which two devices as shown in FIG. 1 stand oppositely, the human to be inspected stands therebetween so that the two devices each scan one side of the human, and thus there is no need for the human to turn around.

Figure 2:
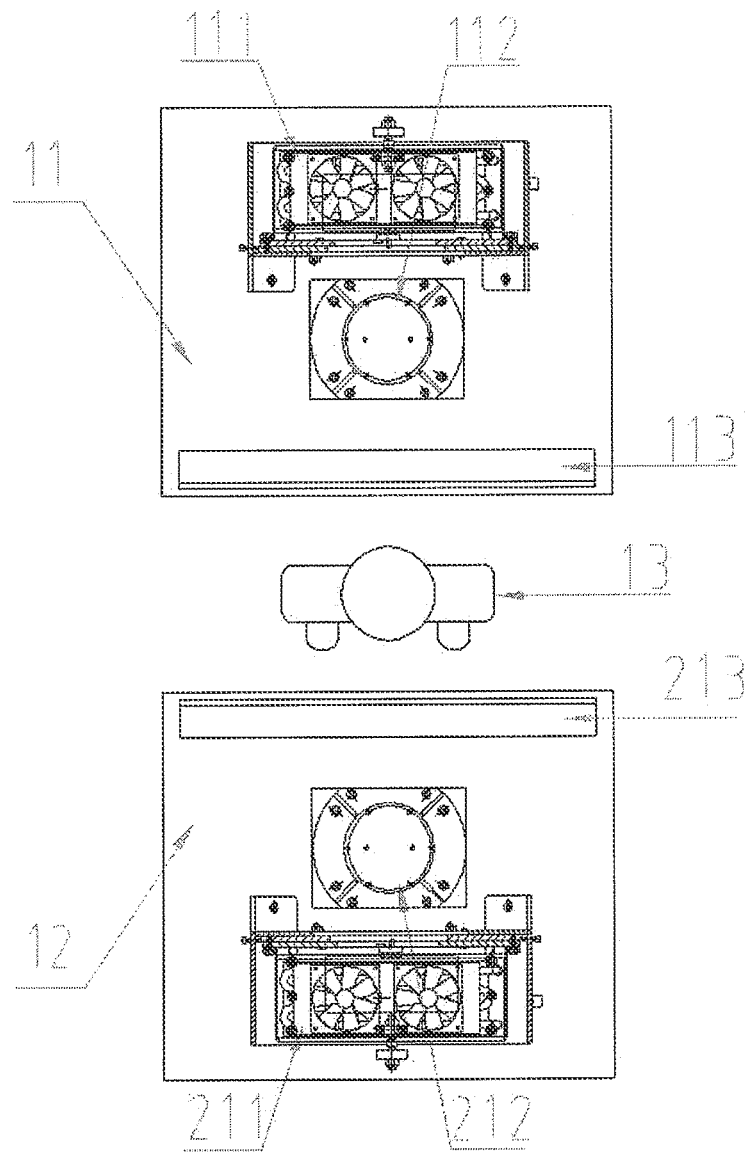
FIG. 2 illustrates a schematic diagram of a human body back-scattering scanning system according to another embodiment of the invention.

FIG. 2 illustrates a top view of a human body back-scattering scanning system according to another embodiment of the invention. The system as shown in FIG. 2 includes first back-scattering scanning device 11 (referred hereunder as "first device" for simplicity) and second back-scattering scanning device 12 (referred hereunder as "second device" for simplicity).

First back-scattering scanning device 11 includes a first X-ray source 111, a first flying-spot forming unit 112 and a first back-scattering detector 11. The second back-scattering scanning device 12 is placed to be opposite to the first back-scattering scanning device 11, and includes a second X-ray source 211, a second flying-spot forming unit 212 and a second back-scattering detector 213. According to some embodiments, the first flying-spot forming unit 112 and the second flying-spot forming unit 212 both may be the flying-spot forming unit as disclosed in Chinese patent application No. CN102565110A. The flying-spot forming units 112 and 212 each may have a cylindrical surface on which holes are distributed spirally. X-rays emitted from the ray sources are modulated by the units having spirally distributed flying-spots and exit in different directions in a time-sharing manner.

Figure 3:
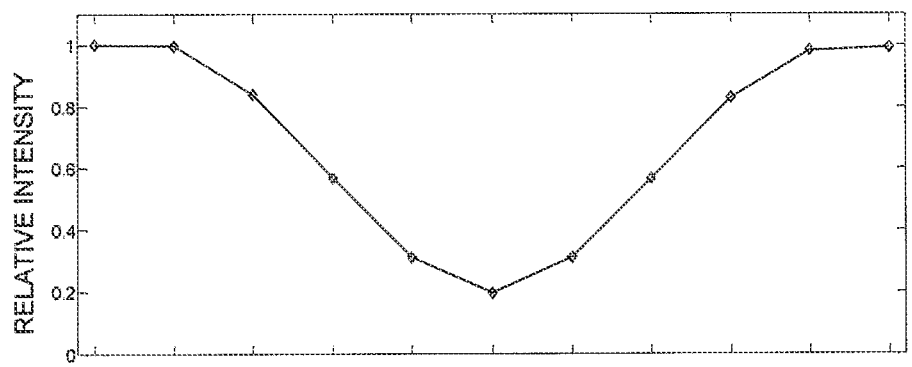
FIG. 3 illustrates a diagram of intensity of beams of X-rays outputted from a flying-spot forming unit varying over time in a cycle according to another embodiment of the invention.

FIG. 3 illustrates a diagram of movement of X-ray spots emitted from a flying-spot forming unit on a surface of a human body. The variation of intensity of X-rays emitted from a flying-spot forming unit during rotation of a cylinder having flying-spots formed thereon is shown in FIG. 3. Only one cycle (from one hole to the next neighboring hole) is shown. It can be seen from FIG. 3 that X-rays modulated by the flying-spot forming unit having spirally distributed flying-spots are not distributed uniformly over time on the irradiated surface; and instead have a distribution having alternating peaks and valleys. In this way, the controlling and data processing terminal 5 precisely controls scanning starting times to cause the second back-scattering scanning device 12 and the first back-scattering scanning device 11 to have scanning starting times that are different by a half of the cycle. That is, the first back-scattering scanning device 11 and the second back-scattering scanning device 12 output the beams of X-rays at different time which is different by a half of the cycle of the intensity of beams varying over time, and thereby the beams outputted from the second back-scattering scanning device 12 are at maximum when the beams outputted from the first back-scattering scanning device 11 are at minimum. In other words, even if the ray source of the second back-scattering scanning device 12 emits rays, it will not significantly affect imaging result of the first back-scattering scanning device 11. In this way, the two devices may emit rays and perform scanning at the same time, and thus the total scanning time is reduced.

In some embodiments, the two back-scattering scanning devices 11 and 12 stand oppositely, and each uses a flying-spot forming unit having a cylinder with holes spirally distributed thereon as disclosed in Chinese patent application No. CN102565110A. The person to be inspected stands between the two devices, with the front facing one device and the back facing the other device.

In some embodiments, the cylinders of the two flying-spot forming unit rotate at the same rate, and the two devices have the same scanning period. The cycle T of intensity of beams varying over time can be calculated according to the rotating rate of the cylinders. Furthermore, the two devices use one and the same controlling system, to have the first back-scattering scanning device 11 start scanning at a time, and have the second back-scattering scanning device 12 start scanning T/2 later, T being a cycle of intensity of beams varying over time. In this way, the two devices can emit beams and perform scanning at the same time.

Figure 4:
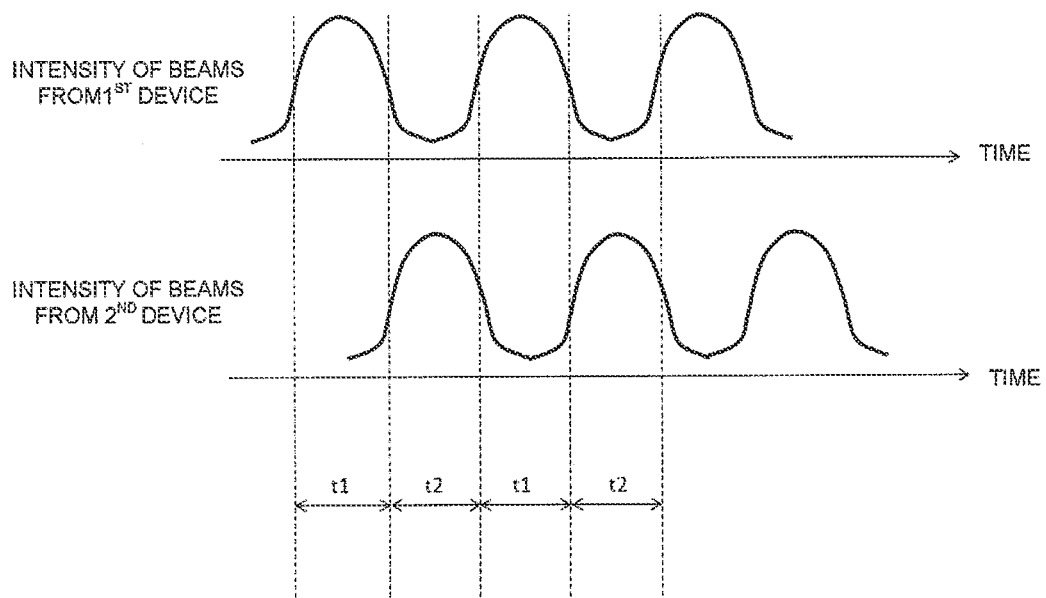
FIG. 4 illustrates a diagram of intensities of beams of X-rays outputted from two flying-spot forming units in two back-scattering scanning devices varying over time according to still another embodiment of the invention.

Preferably, the collecting circuitries downstream from the detectors in the two devices may precisely control the time for collecting signals, to have for example the timing as shown in FIG. 4. In the figure, t1 is the time for collecting signals of device 1, and t2 is the time for collecting signals of device 2. For example, the controlling and data processing terminal 5 further generates signals to cause the back-scattering detector 113 to collect reflected beams of X-rays about the peaks of the beams of X-rays emitted from flying-spot forming unit 112 and cause the back-scattering detector 213 to collect reflected beams of X-rays about the peaks of the beams of X-rays emitted from flying-spot forming unit 212.

The pattern of intensities of beams varying over time as shown in FIG. 4 depends on diameter of holes and space between holes on the cylinders of the flying-spot forming units 112 and 212. Diameter of holes and space between holes may be adjusted so that the beams emitted from the second back-scattering scanning device 12 have a low intensity when the back-scattering detector 113 of the first back-scattering scanning device 11 collects signals. Similarly, they may be adjusted so that the beams emitted from the first back-scattering scanning device 11 have a low intensity when the back-scattering detector 213 of the second back-scattering scanning device 12. In this way, the absorbed amount of signals that make no contribution to the back-scattering signals of human body is reduced.

Figure 5:
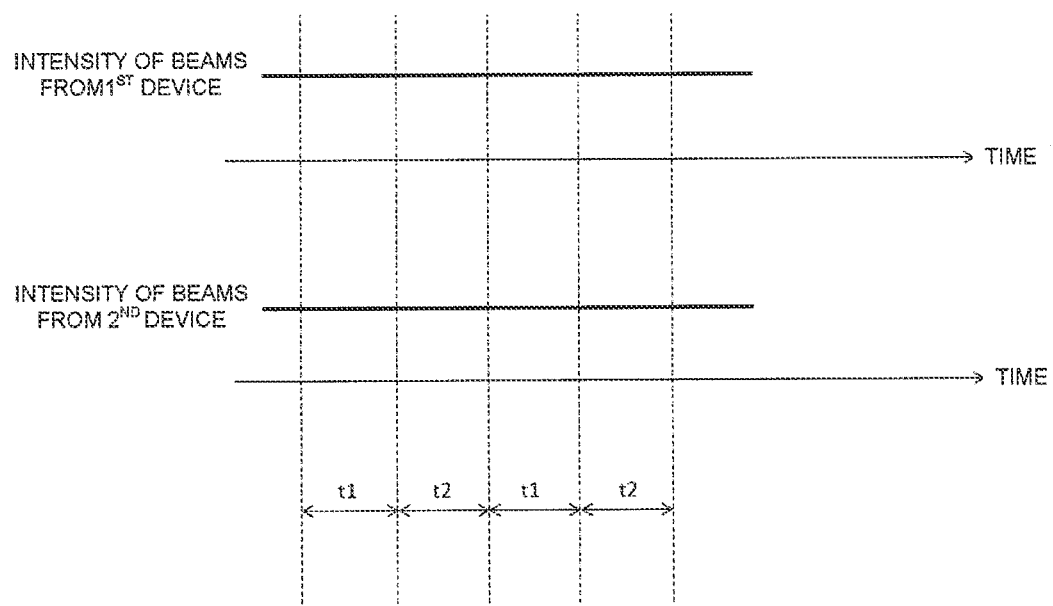
FIG. 5 illustrates a diagram of intensities of beams of X-rays outputted from two flying-spot forming units in two back-scattering scanning devices varying over time according to yet another embodiment of the invention.

In other embodiments, for example in a system having flying-spot forming units of other types, the intensity of beams emitted from the devices may not vary over time, as shown in FIG. 5. In such case, the two devices may still emit rays and perform scanning at the same time by collecting signals in a time-sharing manner. According to some embodiments, the system includes the first back-scattering scanning device 11 and the second back-scattering scanning device 12 which are placed in opposite positions relative to each other so that an object 13 to be inspected stands therebetween when it is to be scanned.

The first back-scattering scanning device 11 includes a first X-ray source 111, a first flying-spot forming unit 112 and a first detector 113. The first flying-spot forming unit 112 outputs beams of X-rays, and the first detector 113 receives beams of X-rays that are reflected from body of the inspected object. The second back-scattering scanning device 12 includes a second X-ray source 211, a second flying-spot forming unit 212 and a second detector 213. The second flying-spot forming unit 212 outputs beams of X-rays, and the second detector 213 receives beams of X-rays that are reflected from body of the inspected object.

The system further includes a controlling unit (for example controlling and data processing terminal 5) that is coupled to the first back-scattering scanning device 11 and the second back-scattering scanning device 12, and configured to generate controlling signals to cause the first and second detectors to collect reflected beams of X-rays in a time-sharing manner. In the system according to embodiments of the invention, half of the absorbed amount of signals with respect to the inspected object makes no contribution to the signals used in imaging. Thus the system obtains a SNR poorer than that of a scanning mechanism by using cylindrical-spirally distributed flying-spots in respect to the same absorbed amount. However, the system has an enhanced scanning speed.

The foregoing detailed description has set forth various embodiments of the human body back-scattering inspection system and methods via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present invention has been described with reference to several typical embodiments, it is apparent to those skilled in the art that the terms are used for illustration and explanation purpose and not for limitation. The present invention may be practiced in various forms without departing from the esprit or essence of the invention. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present invention which is defined by the claims as attached.

What is claimed is:

1. A human body back-scattering inspection system, comprising:
    a first back-scattering scanning device and a second back-scattering scanning device which are placed in opposite positions relative to each other so that an object to be inspected stands therebetween when it is to be scanned, the first back-scattering scanning device comprising a first X-ray source, a first flying-spot forming unit, and a first detector, the first flying-spot forming unit having a plurality of holes that are distributed spirally on its cylindrical surface and outputting beams of X-rays, the first detector receiving beams of X-rays that are reflected from body of the inspected object, the second back-scattering scanning device comprising a second X-ray source, a second flying-spot forming unit, and a second detector, the second flying-spot forming unit having a plurality of holes that are distributed spirally on its cylindrical surface and outputting beams of X-rays, the second detector receiving beams of X-rays that are reflected from body of the inspected object; and
    a controlling unit coupled to the first and second back-scattering scanning devices, and configured to generate controlling signals to cause the first flying-spot forming unit and the second flying-spot forming unit to output the beams of X-rays at time which is different by about a half of a cycle of the intensity of beams varying over time;
    wherein diameter of holes and space between holes on the cylindrical surface of the flying-spot forming units are adjusted to reduce intensity of beams emitted from the second back-scattering scanning device when the first detector collects signals, and reduce intensity of beams emitted from the first back-scattering scanning device when the second detector collects signals.

2. The human body back-scattering inspection system according to claim 1, wherein the controlling unit is configured to generate controlling signals to cause the first and second back-scattering scanning devices to start at time that is different by about a half of a cycle of the intensity of beams varying over time.

3. The human body back-scattering inspection system according to claim 1, wherein the controlling unit is configured to generate controlling signals to cause the first detector to collect only reflected beams of X-rays about peaks of the beams of X-rays emitted from the first flying-spot forming unit, and to cause the second detector to collect only reflected beams of X-rays about peaks of the beams of X-rays emitted from the second flying-spot forming unit.

4. A human body back-scattering inspection system, comprising:
    a first back-scattering scanning device and a second back-scattering scanning device which are placed in opposite positions relative to each other so that an object to be inspected stands therebetween when it is to be scanned, the first back-scattering scanning device comprising a first X-ray source, a first flying-spot forming unit and a first detector, the first flying-spot forming unit outputting beams of X-rays, the first detector receiving beams of X-rays that are reflected from body of the inspected object, the second back-scattering scanning device comprising a second X-ray source, a second flying-spot forming unit and a second detector, the second flying-spot forming unit outputting beams of X-rays, the second detector receiving beams of X-rays that are reflected from body of the inspected object; and
    a controlling unit coupled to the first and second back-scattering scanning devices, and configured to generate controlling signals to cause the first and second detectors to collect reflected beams of X-rays in a time-sharing manner;
    wherein each of the first flying-spot forming unit and the second flying-spot forming unit has a plurality of holes that are distributed spirally on its cylindrical surface and outputs beams of X-rays therefrom;
    wherein diameter of holes and space between holes on the cylindrical surface of the flying-spot forming units are adjusted to reduce intensity of beams emitted from the second back-scattering scanning device when the first detector collects signals, and reduce intensity of beams emitted from the first back-scattering scanning device when the second detector collects signals.

5. A method for use in a human body back-scattering inspection system comprising a first back-scattering scanning device and a second back-scattering scanning device which are placed in opposite positions relative to each other so that an object to be inspected stands therebetween when it is to be scanned, the first back-scattering scanning device comprising a first X-ray source, a first flying-spot forming unit, and a first detector, the first flying-spot forming unit having a plurality of holes that are distributed spirally on its cylindrical surface and outputting beams of X-rays, the first detector receiving beams of X-rays that are reflected from body of the inspected object, the second back-scattering scanning device comprising a second X-ray source, a second flying-spot forming unit, and a second detector, the second flying-spot forming unit having a plurality of holes that are distributed spirally on its cylindrical surface and outputting beams of X-rays, the second detector receiving beams of X-rays that are reflected from body of the inspected object, the method comprising:

generating controlling signals to cause the first flying-spot forming unit and the second flying-spot forming unit to output the beams of X-rays at time which is different by a half of a cycle of the intensity of beams varying over time;

wherein diameter of holes and space between holes on the cylindrical surface of the flying-spot forming units are adjusted to reduce intensity of beams emitted from the second back-scattering scanning device when the first detector collects signals, and reduce intensity of beams emitted from the first back-scattering scanning device when the second detector collects signals.

6. The method according to claim 5, further comprising generating controlling signals to cause the first and second back-scattering scanning devices to start at time that is different by about a half of the cycle of the intensity of beams varying over time.

7. The method according to claim 5, further comprising generating controlling signals to cause the first detector to collect only reflected beams of X-rays about peaks of the beams of X-rays emitted from the first flying-spot forming unit, and to cause the second detector to collect only reflected beams of X-rays about peaks of the beams of X-rays emitted from the second flying-spot forming unit.

8. A method for use in a human body back-scattering inspection system comprising a first back-scattering scanning device and a second back-scattering scanning device which are placed in opposite positions relative to each other so that an object to be inspected stands therebetween when it is to be scanned, the first back-scattering scanning device comprising a first X-ray source, a first flying-spot forming unit, and a first detector, the first flying-spot forming unit outputting beams of X-rays, the first detector receiving beams of X-rays that are reflected from body of the inspected object, the second back-scattering scanning device comprising a second X-ray source, a second flying-spot forming unit, and a second detector, the second flying-spot forming unit outputting beams of X-rays, the second detector receiving beams of X-rays that are reflected from body of the inspected object, wherein each of the first flying-spot forming unit and the second flying-spot forming unit has a plurality of holes that are distributed spirally on its cylindrical surface and outputs beams of X-rays therefrom, the method comprising generating controlling signals to cause the first and second detectors to collect reflected beams of X-rays in a time-sharing manner;

wherein diameter of holes and space between holes on the cylindrical surface of the flying-spot forming units are adjusted to reduce intensity of beams emitted from the second back-scattering scanning device when the first detector collects signals, and reduce intensity of beams emitted from the first back-scattering scanning device when the second detector collects signals.

\* \* \* \* \*